United States Patent [19]

Richardson et al.

[11] Patent Number: 4,972,011

[45] Date of Patent: Nov. 20, 1990

[54] FLAME RETARDANT POLYMER COMPOSITION CONTAINING PHOSPHONIC ACID SALTS

[75] Inventors: Joyce Richardson, Middleton; Richard J. Dellar, Timperley, both of England

[73] Assignee: Ciba-Geigy Corporation, Ardsley, N.Y.

[21] Appl. No.: 407,224

[22] Filed: Sep. 8, 1989

Related U.S. Application Data

[63] Continuation-in-part of Ser. No. 45,021, Apr. 30, 1987, abandoned.

[30] Foreign Application Priority Data

May 9, 1986 [GB] United Kingdom ............... 8611357

[51] Int. Cl.$^5$ ............................................. C08K 5/53
[52] U.S. Cl. ..................................... 524/130; 524/131
[58] Field of Search ............................. 524/130, 131

[56] References Cited

U.S. PATENT DOCUMENTS 3,894,986  7/1975  Racky et al. .................... 524/130
4,113,841  9/1978  Staendeke et al. ............... 423/265
4,383,066  5/1983  Sugio et al. ..................... 524/124

FOREIGN PATENT DOCUMENTS 1004747  1/1985  Japan ............................ 524/130

Primary Examiner—Kriellion Morgan
Attorney, Agent, or Firm—Harry Falber; Bruce M. Collins

[57] ABSTRACT

Compositions comprising a halogen-free polymer and, as flame retardant, at least one aluminum salt of a phosphonic acid of the formula:

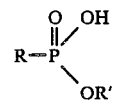

in which R is a straight or branched chain alkyl group having 1 to 3 carbon atoms optionally substituted by one or more of halogen atoms or hydroxyl groups and R' is hydrogen or an alkyl group having 1 to 3 carbon atoms.

13 Claims, No Drawings

FLAME RETARDANT POLYMER COMPOSITION CONTAINING PHOSPHONIC ACID SALTS

CROSS REFERENCE

This is a continuation-in-part of Ser. No. 45,021 filed Apr. 30, 1987, now abandoned.

DETAILED DESCRIPTION

The invention relates to flame retardant polymer compositions containing phosphonic acid salts.

Polymers, particularly halogen-free polymers, are commonly made more flame retardant by incorporating therein a phosphorus-containing compound, a halogen-containing compound or a mixture thereof. Some polymers are processed at high temperatures of, for example, 250° C. or higher, and many known flame retardants are not suitable under these conditions because they are too volatile, or not sufficiently thermally stable. We have now found a class of compounds which are thermally stable at high temperature and which can be used as flame retardants in a wide range of plastics. The compounds also do not given unwanted plasticizing properties to rigid polymers. Accordingly, the present invention provides a composition comprising a halogen-free polymer and as flame retardant at least one aluminum salt of a phosphonic acid of the formula:

$$R-P\underset{OR'}{\overset{O}{\underset{\|}{\diagup}}}\overset{OH}{\diagdown}$$

in which R is a straight or branched chain alkyl group having 1 to 3 carbon atoms optionally substituted by one or more of halogen atoms or hydroxyl groups and R' is H or an alkyl group having 1 to 3 carbon atoms. Halogen atoms in alkyl groups are e.g. fluorine, bromine and chlorine atoms. The following are mentioned as haloalkyl groups R: chloromethyl, bromomethyl, trifluoromethyl, dichloromethyl, dibromomethyl, 2-chloroethyl, 1-chloropropyl and 1-bromopropyl. Alkyl groups R substituted by hydroxyl groups are preferably such groups substituted by one hydroxyl group such as, e.g. hydroxymethyl, 2-hydroxyethyl and 3-hydroxypropyl.

Preferably R represents unsubstituted $C_1$–$C_3$ but most preferably R is methyl. R' is preferably hydrogen or methyl. Particularly preferred are compositions wherein R and R' are each methyl.

The salt may be a simple ionic compound formed between anions of the phosphonic acid and aluminum cations. Where R' is H the salt may have a polymeric structure as represented by the general formula:

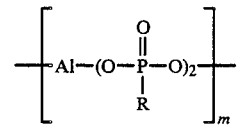

where R is as defined above, m is from 2 to 100, and where each group

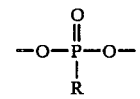

is attached to aluminum atoms only.

Non limiting examples of phosphic acid salts of the present invention are:

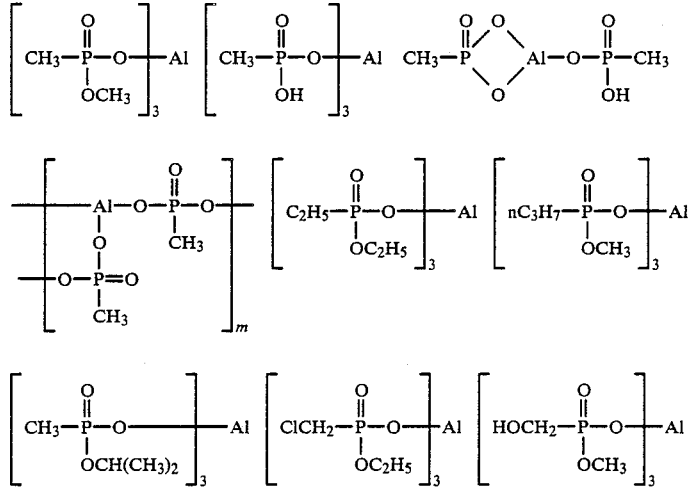

The phosphonic acid salts are either known, or can be readily prepared by known methods. The phosphonic acid or its sodium salt may be reacted with aluminum carbonate.

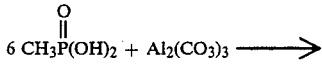

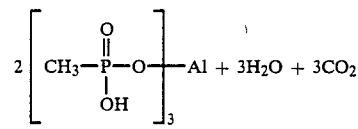

The sodium salt of the phosphonic acid or partial ester may also be reacted in aqueous solution with a water soluble aluminum salt, e.g.

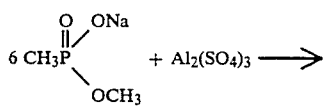

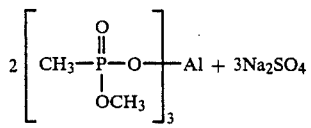

Other processes include reacting an ester of the phosphonic acid with an aluminum halide or aluminium alkoxide, e.g.

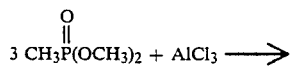

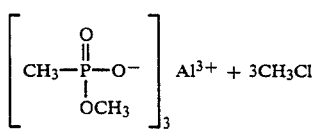

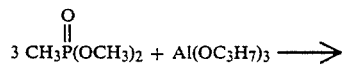

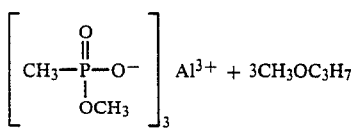

The amount of phosphonic acid salt added to the polymer as a flame retardant may be varied over a wide range. Usually from 0.1 to 100 parts by weight are used per 100 parts by weight of polymer. Preferably there are used 0.5 to 30 parts and, most preferably, from 2 to 20 parts by weight per 100 parts by weight of polymer. The optimum amount used depends on the nature of the polymer and the actual salt used and may be readily determined by simple experiment. However, because the salts are generally effective at low levels of addition they produce less unwanted effects in the polymer than other known flame retardant additives.

The salts may be used in various physical forms depending on the polymer used and the desired properties. For instance, the salts may be ground to a finely divided form to enable better dispersion throughout the polymer.

The phosphonic acid salts may be used in various polymers.

Examples of polymers which may be rendered flame retardant are:

1. Polyphenylene oxides and sulfides, and blends of these polymers with polystyrene graft polymers or styrene copolymers such as high impact polystyrene, EPDM copolymers with rubbers, as well as blends of polyphenylene oxide with polyamides and polyesters.

2. Polyurethanes which are derived from polyethers, polyesters or polybutadiene with terminal hydroxyl qroups on the one side and aliphatic or aromatic polyisocyanates on the other side including polyisocyanurates, as well as precursors thereof.

3. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance, with polyethylene glycol, polypropylene glycol or polytetramethylene glycols.

4. Polyesters which are derived from dicarboxylic acids and dialcohols and/or from hydroxycarboxylic acids or the corresponding lactones, such as polyethylene terephthalate, polybutylene terephthalate, poly-1,4-dimethylol-cyclohexane terephthalate and polyhydroxybenzoates as well as block-copolyether-esters derived from polyethers having hydroxyl end groups.

5. Unsaturated polyester resins which are derived from copolyesters of saturated and unsaturated dicarboxylic acids with polyhydric alcohols and vinyl compounds as cross-linking agents.

6. Polystyrene.

7. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/-butadiene copolymers, as well as mixture thereof with random copolymers of styrene or alpha-methylstyrene with dienes or acrylic derivatives, for instance the terpolymers of styrene known as ABS, MBS, ASA or AES terpolymers.

8. Cross-linked epoxide resins which are derived from polyepoxides, for example, from bis-glycidyl ethers, especially bisphenol A diglycidyl ethers, or from cycloaliphatic diepoxides.

9. Polycarbonates.

The compositions of the invention may also contain other conventional ingredients, such as heat stabilizers, light stabilizers, ultra-violet light absorbers, anti-oxidants, anti-static agents, preservatives, adhesion promoters, fillers, pigments, lubricants, blowing agents, fungicides, plasticizers, processing aids, other fire-retardant additives, and smoke suppressants.

Other fire retardant additives which may be used with the phosphonic acid salts include phosphorus containing esters and salts such as triaryl phosphates, alkyl aryl phosphates and ammonium polyphosphate, halogen-, especially bromine- and chlorine-, containing compounds such as decabromodiphenyl ether, hexachlorocyclopentadiene, brominated polystyrene, haloalkyl phosphate and phosphonate esters, antimony oxide, hydrated alumina, bismuth oxide, molybdenum oxide, or mixtures of these compounds with zinc and/or magnesium oxide or salts.

The invention is illustrated by the following Examples. Parts are parts by weight unless indicated otherwise.

EXAMPLE A 28.7 g (0.215 mole) anhydrous aluminium chloride are added in portions to 160 g (1.29 moles) dimethyl methyl phosphonate with ice/water bath cooling to maintain the temperature at <60° C. On the completion of the addition the temperature is slowly raised to 140° C. over 1 hour and maintained thus for a further 2 hours after which the reaction mixture is cooled at 25° C. and diluted with 200 mls acetone. The white crystalline reaction product is isolated by filtration, washed with 2 x 100 mls acetone and dried under vacuum at 50° C. There are obtained 62.5 g of product having melting point >250° C. and having the following elemental analysis: C: 19.97%; H: 5.08%; Al: 7.37% and P: 25.97%. Calculated for $C_6H_{18}AlO_9P_3$: C: 20.34%; H: 5.08%; Al: 7.63% and P: 26.27%.

EXAMPLE B

A solution of 57.6 g (0.6 moles) methylphosphonic acid in 70 mls of deionized water is added dropwise to a suspension of 23.4 g (0.10 moles) of aluminium carbonate in 300 mls of deionized water at ambient temperatures. The reaction mixture is stirred for 1 hour and then heated at reflux temperature for a further 4 hours, cooled and filtered. Concentration of the filtrate to dryness gives a colorless solid with melting point 187°–192° C., and having elemental analysis: C: 11.03%; H: 3.87%; P: 28.74%. Calculated for $C_3H_{12}AlO_9P_3 \cdot H_2O$: C: 10.91%; H: 4.24%; P: 28.18%.

EXAMPLE C

Using the procedure described in Example A, reaction of 83 g (0.5 moles) diethylethylphosphonate with 13.4 g (0.1 moles) of anhydrous aluminium chloride gives 35 g of a colorless solid with melting point >250° C., and having elemental analysis: C: 31.80%; H: 6.59%; P: 21.29%; Al: 6.14%. Calculated for $C_{12}H_{30}AlO_9P_3$: C: 32.80%; H: 6.85%; P: 21.23%; Al: 6.16%.

EXAMPLE D

Using the procedure described in Example A, reaction of 152 g (1.0 mole) dimethylpropylphosphonate with 26.7 g (0.2 moles) of anhydrous aluminium chloride gives 88.5 g of a colorless solid with melting point >250° C., and having elemental analysis: C: 32.74%; H: 7.13%; P: 21.48%; Al: 5.64%. Calculated for $C_{12}H_{30}AlO_9P_3$: C: 32.80%; H: 6.85%; P: 21.23%; Al: 6.16%.

EXAMPLE E

Using the procedure described in Example A, reaction of 149.2 g (0.8 moles) diethylchloromethylphosphonate with 26.7 g (0.2 moles) of anhydrous aluminium chloride gives 86.3 g of a colorless solid with melting point >250° C., and having elemental analysis: C: 21.08%; H: 4.15%; P: 18.41%; Cl: 21.61%; Al: 5.50%. Calculated for $C_9H_{21}AlCl_3O_9P_3$: C: 21.62%; H: 4.20%; P: 18.62%; Cl: 21.32%; Al: 5.41%.

EXAMPLE F

Using the procedure described in Example A, reaction of 168 g (1.0 moles) diethylhydroxymethylphosphonate with 26.7 g (0.2 moles) of anhydrous aluminium chloride gives 64.6 g of a colorless solid with melting point >250° C., and having elemental analysis: C: 24.38%; H: 5.44%; P: 20.33%; Al: 5.93%. Calculated for $C_9H_{24}AlO_{12}P_3$: C: 24.32%; H: 5.41%; P: 20.95%; Al: 6.08%.

EXAMPLE G

Using the procedure described in Example A, reaction of 54.0 g (0.3 moles) diisopropylmethylphosphonate with 13.4 g (0.1 moles) of anhydrous aluminium chloride gives 18.0 g of a colorless solid with melting point >250° C., and having elemental analysis: C: 32.20%; H: 7.02%; P: 21.21%; Al: 6.01%. Calculated for $C_{12}H_{30}AlO_9P_3$: C: 32.80%; H: 6.85%; P: 21.23%; Al: 6.16%.

EXAMPLE H

Compositions are made up by melt compounding at a temperature of 230° C. 100 parts by weight of the plastics based on polystyrene and polyphenylene oxide, sold under the Trade name Noryl ® (General Electric), and 12 parts by weight of the salt indicated in Table 1.

The Oxygen Index (O/I) is measured according to BS.2782: part 1: method 141A:1983 and the flammability tested according to the "Test for Flammability of Plastics Materials - UL 94", Feb, 1, 1984. The results are shown in Table 1.

TABLE 1

| Salt from Example | OI % | UL 94 |
|---|---|---|
| None | 22.3 | HB |
| A | 28.2 | VE 0 |
| B | 27.3 | VE 1 |
| C | 25.2 | VE 1 |
| D | 26.9 | VE 0 |
| E | 26.0 | VE 1 |
| F | 24.4 | VE 2 |
| G | 25.5 | VE 2 |

These results show the flame retardant effect of the aluminum salts by virtue of an increase in OI and a higher rating in the UL 94 test, where VE 0 is the highest rating followed by VE 1, then VE 2 and finally HB (complete burning of sample).

EXAMPLE I

Compositions are made up by melt compounding at a temperature of 270° C. 100 parts by weight of Nylon 66 and 12 parts by weight of the aluminum salt indicated in Table 2. The OI and UL 94 tests are carried out as in Example H.

TABLE 2

| Salt from Example | OI % | UL 94 |
|---|---|---|
| None | 21.3 | HB |
| A | 24.7 | VE 2 |
| D | 22.4 | VE 2 |

EXAMPLE J

Compositions are made up by melt compounding at a temperature of 270° C. 100 parts by weight of polybutylene terephthalate and 12 parts by weight of the aluminum salt indicated in Table 3. The OI and UL 94 tests are carried out as in Example H.

TABLE 3

| Salt from Example | OI % | UL 94 |
|---|---|---|
| None | 19.0 | HB |
| A | 22.5 | VE 2 |
| D | 20.9 | VE 2 |

EXAMPLE K the following foam formulation is utilized to shown the effect of flame retardant.

| Reactant | Concentration (parts by weight) |
|---|---|
| Thanol R650x ® (aromatic polyol manufactured and sold by Texaco Chemicals Co.) | 100 |

-continued

| Reactant | Concentration (parts by weight) |
|---|---|
| Water | 0.2 |
| Silicone surfactant | 2 |
| (Polyurax ® SR 393, sold by BP Chemicals) | |
| Trichlorofluoromethane | 40 (to foam density 30 kg/m$^3$) |
| Flame retardant salt | 10 |
| Suprasec DND ® (polymeric diphenylmethane diisocyanate manufactured and sold by ICI) | to index of 1.05 |

The above ingredients are mixed together for 10 seconds in a high speed stirrer (2000 rpm) at room temperature, with the isocyanate being added last, and then poured immediately into a cardboard mold. The exothermic reaction which ensues is allowed to free rise the foam. The length of time from the addition of the isocyanate to the formation of a creamy consistency of the mixture is given as the cream time. the time required for the foam to attain the maximum height is given as the rise time. The time until the foam is no longer tacky is designated as the non-tack time. After attainment of the non-tack time, the foam is aged for 3 days at ambient temperature.

The specimens are cut from the foam after 3 days storage and subjected to the limiting Oxygen Index Test and DIN 4102 B2 vertical Burn Test. Results are shown in Table 4.

TABLE 4

| | Foam Parameters | | | | DIN 4012 B2 Test | | |
|---|---|---|---|---|---|---|---|
| Salt from Example | Cream Time (sec.) | Rise Time (sec.) | Non-Tack Time (sec.) | OI % | Time to Spec. Mark (sec.) | Max Flame Height (cm) | Burn Time (sec.) |
| None | 17 | 70 | 120 | <21.0 | 3 | >20 | >60* |
| A | 16 | 57 | 104 | 23.7 | — | 14 | 12 |

*Burns completely

EXAMPLE L 100 parts of high impact polystyrene polymer (Shell 581) and 12 parts of the salt of Example A are mixed and extruded at 180° C. The following results are obtained:

| High impact polystyrene | OI % | UL 94 |
|---|---|---|
| Blank | 17.3 | Full burn |
| + salt from Example A | 18.4 | V2 |

EXAMPLE M 100 parts of ABS polymer (Cycolac T) are mixed with 12 parts of the salt of Example A and the mixture extruded and pressed at 180° C. The following results are obtained:

| ABS | OI % |
|---|---|
| Blank | 16.8 |
| + salt from Example A | 20.3 |

EXAMPLE N 100 parts of millable polyurethane, identified below, are mixed with 12 parts of the salt from Example A and milled at 180° C. The following results are obtained:

| PU Elastomer | OI % |
|---|---|
| Estane 58300 ® (B.F. Goodrich Co.) | 20.2 |
| + salt from Example A | 22.4 |
| Estane 54600 ® (B.F. Goodrich Co.) | 20.2 |
| + salt from Example A | 22.2 |

EXAMPLE O 100 parts of a general purpose non-halogen containing unsaturated polyester (ex Jotun) are mixed with 12 parts of the salt from Example A and 1 part methyl ethyl ketone peroxide and cured at room temperature. The following results are obtained:

| Polymer | OI % |
|---|---|
| Blank | 18.4 |
| + salt from Example A | 21.4 |

EXAMPLE P 100 parts of diglycidyl ether of bisphenol A (with epoxy content of 5.3 equivalent/kg) is mixed at 25° C. with 22 parts of TMD (equal parts of 2,2,4-trimethyl hexamethylenediamine and 2,4,4-trimethylhexamethylene diamine) together with 40 parts of the salt from Example A. The reaction mixture is degassed at 25° C., poured into a suitable casting mold, allowed to stand 18 hours at 25° C. and is finally heated for 1 hour at 100° C. The end product is an opaque solid. The following results are obtained:

| Polymer | OI % | UL 94 |
|---|---|---|
| Blank | 22.4 | Full burn |
| + salt from Example A | 26.0 | V2 |

EXAMPLE Q 100 parts of an epoxy resin derived from Bisphenol A having an epoxide content of 2.4 equiv./kg are mixed at 135° C. with 30 parts of silica and 40 parts of the product from Example A. The resulting mixture is cast and then heated for 16 hours at 135° C. The cured product is an opaque solid which does not ignite when a flame is applied to it. The following results are obtained.

| Polymer | OI % | UL 94 |
|---|---|---|
| Blank (with CaCO$_3$ instead of product from Example A) | 21 | Full burn |
| + salt from Example A | 39.4 | VO |

What is claimed is:

1. The method of imparting flame retardant properties to a halogen-free polymer which comprises incorporating therein from 0.1 to 100% by weight of polymer of an aluminum salt of a phosphonic acid of the formula:

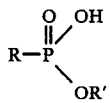

in which R is methyl, ethyl, propyl or isopropyl, unsubstituted or substituted by one or more halo or hydroxy groups; and R' is hydrogen, methyl, ethyl, propyl, or isopropyl.

2. The method according to claim 1 wherein R is methyl, ethyl, propyl or isopropyl.

3. The method according to claim 2 wherein R is methyl.

4. The method according to claim 1 wherein R' is hydrogen or methyl.

5. The method according to claim 1 wherein each of R and R' is methyl.

6. The method according to claim 1 wherein from 2 to 20% by weight of said salt is incorporated.

7. A flame retardant composition comprising a halogen-free polymer and from 0.1 to 100% by weight of polymer of an aluminum salt of a phosphonic acid of the formula:

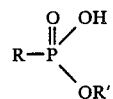

in which R is methyl, ethyl, propyl or isopropyl, unsubstituted or substituted by one or more halo or hydroxy groups; and R' is hydrogen, methyl, ethyl, propyl, or iso-. propyl.

8. A composition according to claim 7 wherein R is methyl, ethyl, propyl or isopropyl.

9. A composition according to claim 8 wherein R is methyl.

10. A composition according to claim 7 wherein R' is hydrogen or methyl.

11. A composition according to claim 7 wherein each of R and R' is methyl.

12. A composition according to claim 7 wherein from 2 to 20% by weight of said salt is present.

13. A composition according to claim 7 in which the polymer is a polyphenylene oxide or sulphide, or a blend thereof with a polystyrene graft polymer or a styrene copolymer, a polyurethane or polyisocyanurate, a polyamide or copolyamide, a polyester or unsaturated polyester, a polystyrene, a graft copolymer of styrene or a terpolymer of styrene, a cross-linked epoxide resin, or a polycarbonate.

* * * * *